United States Patent [19]

Haaks

[11] Patent Number: 5,347,570

[45] Date of Patent: Sep. 13, 1994

[54] METHOD FOR PERIPHERAL ANGIOGRAPHY AND ARRANGEMENT FOR CARRYING OUT THE METHOD

[75] Inventor: Wilfried Haaks, Hamburg, Fed. Rep. of Germany

[73] Assignee: U.S. Philips Corporation, New York, N.Y.

[21] Appl. No.: 80,274

[22] Filed: Jun. 21, 1993

[30] Foreign Application Priority Data

Jun. 20, 1992 [DE] Fed. Rep. of Germany ....... 4220282

[51] Int. Cl.$^5$ .............................................. H05G 1/64
[52] U.S. Cl. ................................ 378/98.12; 378/98.11
[58] Field of Search .................. 378/98.11, 98.12, 98.2, 378/95

[56] References Cited

U.S. PATENT DOCUMENTS

| | | | |
|---|---|---|---|
| 4,551,800 | 11/1985 | Riederer et al. | 378/98.12 X |
| 4,613,983 | 9/1986 | Yedid et al. | 378/98.12 |
| 4,633,307 | 12/1986 | Honda | 378/98.12 X |
| 4,723,261 | 2/1988 | Janssen et al. | 378/98.12 X |
| 4,941,169 | 7/1990 | Kawai et al. | 378/98.12 |
| 4,943,987 | 7/1990 | Asahina et al. | 378/98.12 X |
| 4,995,064 | 2/1991 | Wilson et al. | 378/98.12 |

FOREIGN PATENT DOCUMENTS 3919473 12/1990 Fed. Rep. of Germany .

Primary Examiner—David P. Porta
Attorney, Agent, or Firm—Jack D. Slobod

[57] ABSTRACT

The invention relates to a method for peripheral angiography in which the examination zone and an X-ray imaging system are displaced relative to one another and X-ray images of neighbouring parts of the examination zone are formed in different positions, a contrast image and a mask image being acquired from the X-ray images, and the contrast image and the mask image being subtracted from one another; the invention also relates to an arrangement for carrying out the method. Improved geometrical correspondence between the contrast image and the mask image is achieved in accordance with the invention in that, after contrast medium injection, the displacement is controlled so that the contrast medium bolus is always reproduced in the X-ray images and that the contrast image is acquired from the X-ray image lines which already reproduce the contrast medium whereas the mask image is acquired from the parts of the X-ray images which do not yet reproduce the contrast medium.

6 Claims, 2 Drawing Sheets

METHOD FOR PERIPHERAL ANGIOGRAPHY AND ARRANGEMENT FOR CARRYING OUT THE METHOD

The invention relates to a method for peripheral angiography in which the examination zone and an X-ray imaging system are shifted relative to one another, X-ray images of neighbouring parts of the examination zone being formed in different positions, a contrast image and a mask image being acquired from the X-ray images and the contrast image and the mask image being subtracted from one another, and also relates to an arrangement for carrying out the method.

A method and an arrangement of the kind set forth are known from DE-PS 39 19 473. The contrast image and the mask image are acquired during successive exposures. In order to acquire the mask image, neighbouring parts of, for example a leg are imaged without injection of a contrast medium. During a second exposure, after injection of a contrast medium, X-ray images are made of the same parts so as to acquire a contrast image.

In the ideal case the difference between the contrast image and the mask image resides only in the fact that in the contrast image the vascular system is emphasized by the injected contrast medium. By subtracting the two images from one another, an image of the vascular system is obtained in which the superposed structures, for example bones have been eliminated.

The advantage of such a subtraction angiography method over conventional angiography method consists in that high-contrast (subtraction) images can be formed using a low contrast medium concentration. A drawback of the known method consists in that inadequate geometrical correspondence between the mask image and the contrast image may occur when the patient moves during the period elapsing between the X-ray exposures for the mask image and the X-ray exposures for the contrast image. Such a non-reproducible motion can already occur, for example when the patient, or the top of the patient table, is displaced to the various exposure positions.

It is an object of the invention to provide a method which better ensures that the contrast image and the mask image correspond. This object is achieved in accordance with the invention in that after injection of contrast medium the displacement is controlled so that the contrast medium bolus remains reproduced in the X-ray images, and that the contrast image is acquired from the X-ray image lines which already reproduce the contrast medium whereas the mask image is acquired from the parts of the X-ray images which do not yet reproduce the contrast medium.

When the contrast medium bolus, i.e. the front of the contrast medium in the propagation direction, is imaged in each X-ray image, the X-ray imaging system always supplies lines in which the contrast medium is reproduced and lines in which it is not yet reproduced.

In accordance with the invention, the image lines supplied by the X-ray imaging system in which the contrast medium can already be recognized are used to generate the contrast image, and the image lines which do not yet show contrast medium are used to generate the mask image. Contrast image and mask image are thus composed of image lines which originate from the same X-ray image or from successive X-ray images. Because of the small or even non-existent difference in time between these exposures, the risk of geometrical non-correspondence of contrast image and mask image due to patient motions is substantially reduced. Moreover, the method is faster, because contrast image and mask image can be acquired from a single series of X-ray exposures.

An arrangement for carrying out the method in accordance with the invention, comprising a patient table and an X-ray imaging system for forming X-ray images as well as a drive for displacing the patient table relative to the X-ray imaging system, is characterized in that it comprises:
control means for controlling the instant of exposure and/or of drive so that the contrast medium bolus is reproduced in the X-ray images,
a first memory for storing the lines without contrast medium and a second memory for storing lines with contrast medium, and
a unit which forms the mask image from the image lines in the first memory and the contrast image from the image lines in the second memory.

A further embodiment of the invention comprises a display unit for observing the contrast medium flow and means for controlling the drive and/or the exposure instant by the user. This embodiment enables the user to control, while observing the contrast medium flow, the exposure instant (with a predetermined speed of the relative displacement between X-ray imaging system and examination zone), the speed (with a predetermined instant), or both together, in such a manner that the contrast medium bolus, i.e. the foremost part of the contrast medium in the propagation direction, is imaged preferably at the centre of the X-ray image, viewed in the propagation direction.

When the displacement direction extends at least approximately perpendicularly to the direction of the lines, the area of the patient which is imaged during a (first) X-ray exposure and no longer imaged during the subsequent (second) X-ray exposure will be filled with contrast medium. The lines of the first X-ray image which are associated with this area are stored in the memory for the contrast image. Similarly, the same number of lines of the second X-ray image, associated with the area not yet covered by the first X-ray exposure, are stored in the memory for the mask image, because the contrast medium has not yet reached this area upon the second X-ray exposure. Image interpretation means are not required, so that the device is simplified and less expensive.

A further embodiment of the invention comprises means for determining the contrast medium speed from successive X-ray images and for determining the exposure instant and/or the speed of the drive for the next X-ray exposure. The contrast medium speed can be determined from the last two X-ray images by dividing the displacement of the contrast medium bolus by the distance in time between the last two exposures. The speed of the contrast medium bolus is obtained from the displacement of the contrast medium bolus within these images and the relative displacement between the examination zone and the X-ray imaging system, each time between the penultimate image and the last image. These parameters can be determined by image interpretation means for the detection of the contrast medium boundary, so that the exposure instant, or the table top speed, can be automatically adapted to the contrast medium speed. When the X-ray images are formed with a constant exposure frequency, merely the speed of the relative displacement between examination zone and X-ray imaging system, or the magnitude of the displacement until the next X-ray exposure, need be controlled.

In order to enable accurate determination of the relative displacement between examination zone and X-ray imaging system for successive X-ray exposures, in an embodiment of the invention markers are provided in the beam path of the X-ray imaging system, which markers can be imaged in an X-ray image. The markers can be provided, for example in the table on which the patient is positioned. They are suitably shaped so that their position in the X-ray images can be readily determined by means of an automatic evaluation method so as to be used for geometrically correct acquisition of the mask image or the contrast image from parts of each of the X-ray images.

The invention will be described in detail hereinafter with reference to the drawings. Therein:

Figure 1:
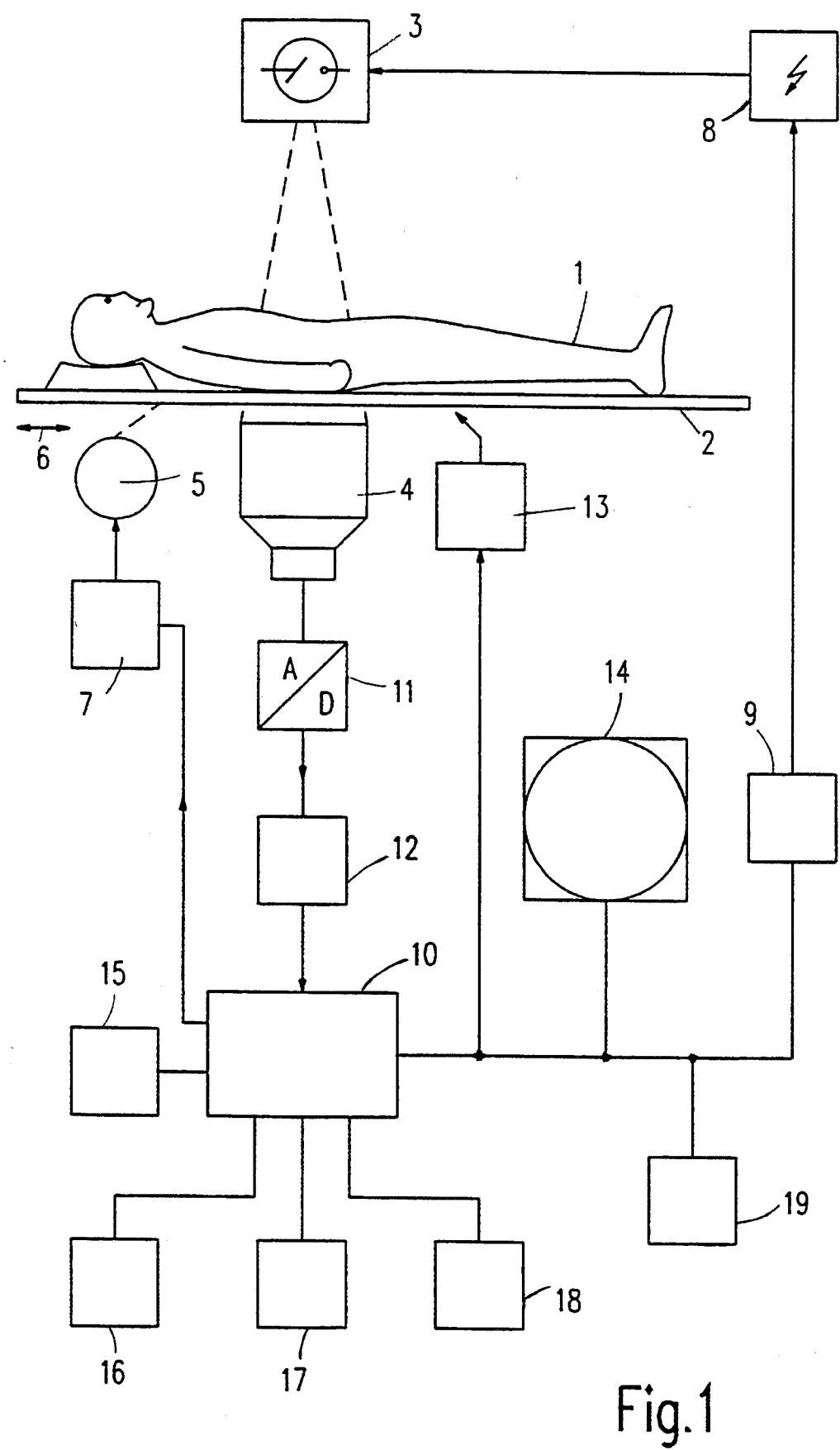
FIG. 1 shows an X-ray examination device for peripheral angiography.

The reference numeral 1 in FIG. 1 denotes a patient to be examined who is positioned on a patient table, only the table top 2 of which is shown. The examination zone is defined by the position of the table top 2 relative to an X-ray imaging system which consists of an X-ray source 3 and an X-ray image converter 4, for example an image intensifier/television chain. The examination zone can be displaced relative to the X-ray imaging system 3, 4. To this end, there is provided a motor 5 which is capable of displacing the table top 2 in its longitudinal direction, i.e. in the direction of the double arrow 6. The motor 5 is controlled by a motor controller 7.

The X-ray source 3 is connected to an X-ray generator 8 which allows for continuous fluoroscopy as well as X-ray exposures with increased intensity. The instant and the parameters of these X-ray exposures are determined by an exposure unit 9 which itself is controlled by an image processing and control unit 10.

The X-ray image converter 4 supplies electric signals which line-wise reproduce the X-ray image or the X-ray fluoroscopic image. The line direction preferably extends perpendicularly to the longitudinal direction of the patient table and hence perpendicularly to the plane of drawing. The analog signal produced by the X-ray image converter 4 is converted into a series of digital data words by an analog-to-digital converter 11. The data stream thus generated is applied, via a buffer memory 12 which enables the buffering of several image lines, to the image processing and control unit 10.

The unit 10 controls inter alia the motor controller 7 and a contrast medium injector 13 whereby a contrast medium can be administered to the patient 1. A monitor 14, connected to the unit 10, enables the propagation of the contrast medium to be followed. Using a control unit 15 connected to the unit 10, the user can also manually preset various examination parameters, for example the speed of the patient table displacement or the trigger instants for the X-ray exposures.

The image processing and control unit acts on an image memory 16 for a contrast image and an image memory 17 for a mask image. Subtraction images can be stored in a digital file 18 or be output as a film image to a film output unit 19.

Figure 2:
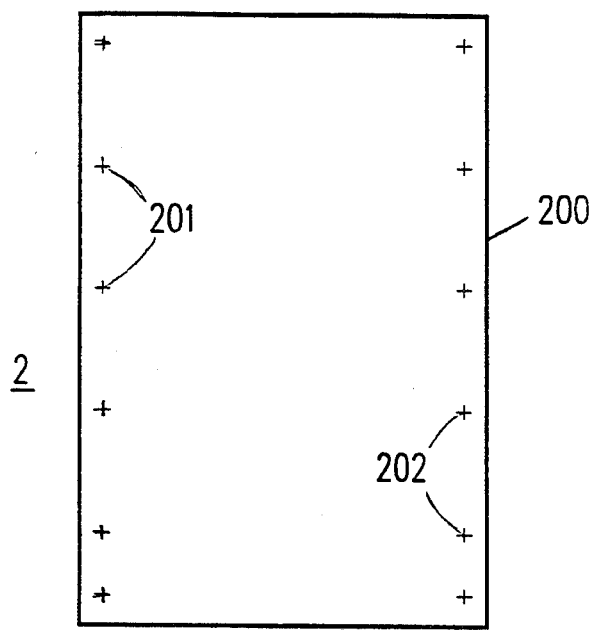
FIG. 2 shows a part of the device.

FIG. 2 represents an X-ray image of the table top 2. Along the edge 200 of the table top there are provided two groups of markers 201 and 202 which strongly absorb the X-rays and which are arranged along straight lines extending parallel to the longitudinal direction of the table, each marker 201 and 202 preferably defining a respective line perpendicular to the longitudinal direction of the table. The markers may consist of a suitable metal and be shaped so that they can be quickly and reliably detected in an X-ray image by means of simple image processing algorithms. They are situated so that in any position of the table top at least one marker is reproduced in the X-ray image.

An angiographic examination will be described in detail hereinafter, it being assumed that the input format of the X-ray image converter 4 is not sufficient to cover the entire area to be examined (leg). The examination starts with an injection of a contrast medium by the contrast medium injector 13. As soon as the contrast medium starts to propagate, the motor controller 7 starts the displacement of the table top in the direction of the head end, so that a leg of the patient is section-wise recorded as far as the foot. The table top speed is adapted to the propagation speed of the contrast medium, so that in the ideal case the position of the contrast medium bolus remains the same in the individual X-ray images, the bolus preferably being imaged at the centre of the X-ray image.

The X-ray images preferably succeed one another with a constant image frequency. This frequency must be chosen so that also in the case of the highest propagation speed of the contrast medium the displacement between two successive X-ray exposures is smaller than half the height of an X-ray image (the height is the dimension of an X-ray image in the displacement direction). At lower image frequencies, gaps could occur in the mask image or the contrast image acquired from the X-ray images.

Figure 3A:
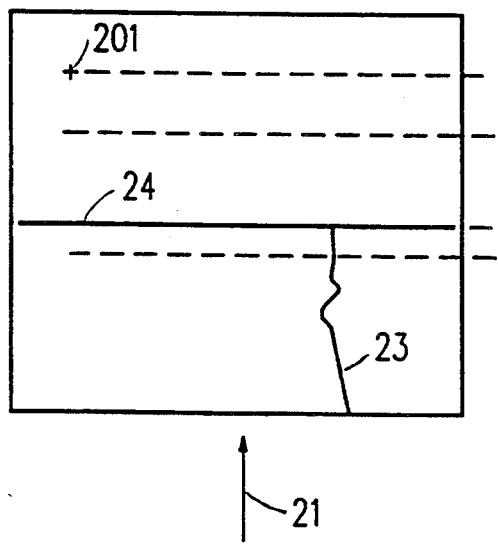
FIGS. 3a and 3b show two successive X-ray images of the vascular system.
Figure 3B:
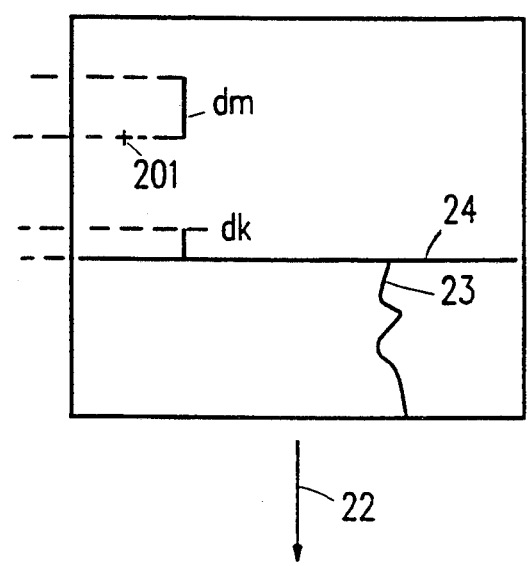

FIGS. 3a and 3b show two images, the image according to FIG. 3b directly succeeding the image according to FIG. 3a. In both X-ray images all anatomical details have been omitted for the sake of clarity, except for a vessel 23 filled with contrast medium. The propagation direction of the contrast medium is denoted by the arrow 21 (FIG. 3a), whereas the oppositely directed arrow 22 (FIG. 3b) indicates the direction of displacement of the table top. The line on which the contrast medium bolus is situated is represented by the solid line 24 in both X-ray images.

Assuming that the lines succeed one another from the bottom upwards during the scanning of the individual X-ray images, the first lines will be situated in the part of the X-ray image in which the vessel 23 filled with contrast medium is also situated. These lines are written into the memory 16 for the contrast image. During the writing of the lines, the image processing unit 10 checks whether contrast medium, or a vessel filled with contrast medium, is still present in the relevant line. If so, the line is written into the memory 16. When the contrast medium boundary (line 24), or a plurality of successive lines without a vessel filled with contrast medium, have been detected, these and all further lines of the X-ray image are loaded into the image memory 17 for the mask image. Geometrical assignment is facilitated by detection of the marker 201 in the X-ray image.

The detection of lines with and without contrast medium can be performed by way of utilizing known pattern recognition methods which suppress the large structures (bones) in the image and which emphasize structures of small dimensions (for example, vessels). In order to increase the reliability, if necessary it can also be checked whether the positions determined for a vessel filled with contrast medium are approximately the same in both lines.

The operations for forming the next image (FIG. 3b) are the same, some lines being added at the upper image edge (at the side of the feet) due to the movement of the table top, whereas the same number of lines is eliminated at the lower image edge (at the side of the head).

Due to the displacement of the table top between the two X-ray exposures, the image of the marker 201 will no longer be situated in the same line as in FIG. 3a, but in a line which has been shifted dm lines towards the bottom. The line z in the X-ray image shown in FIG. 3a and the line z-dm in the X-ray image shown in FIG. 3b (the lines being counted from the bottom upwards) thus concern the same anatomical area. If these two lines in the two single images are not situated to different sides of the contrast medium boundary 24, they appear twice in one of the image memories. Therefore, either one of these lines is removed or, better still, pixel-wise added to the other line so as to enable averaging.

The subsequent images are similarly processed, so that gradually a mask image of the leg (without contrast medium) is formed in the image memory 17 and gradually a contrast image is formed in the image memory 16.

As has already been stated, it is important that the line 24 (i.e. the contrast medium boundary) always remains within the image, preferably in a fixed position, for example the centre of the image. This can be achieved by suitably varying the speed of displacement of the table top under visual control by means of the monitor 14. However, it is also possible to adapt the speed automatically when the contrast medium speed between an exposure and the preceding exposure is preset as a reference value for the displacement speed of the table top until the next X-ray exposure. Because the distances in time between the X-ray exposures do not change, it is merely necessary to determine the absolute displacement of the contrast medium from the two successive exposures.

When in the X-ray images shown in the FIGS. 3a and 3b k1 and k2 denote the lines on which the contrast medium boundary 24 is situated, the absolute displacement d (expressed in number of lines) is $$d = dm - dk,$$

where $dk = k1 - k2$. The image processing and control unit 10 determines the speed of displacement from the absolute displacement d thus calculated and the period of time elapsing between two X-ray exposures, and applies this value as a reference value to the motor controller 7. Generally speaking, the position of the contrast medium boundary in the image will also change in the case of such automatic speed control, but this change of position will be comparatively small because the variation of the contrast medium speed between successive X-ray exposures is comparatively small.

After a contrast image and a mask image have thus been formed in the image memories 16 and 17, respectively, a subtraction image can subsequently be calculated for an arbitrary part of the examination zone by pixel-wise forming the difference between the contrast image and the mask image for the relevant part. This image can be output on the monitor 14 or the display screen output unit 19 or be transferred to the file memory 18.

As appears from the foregoing, the markers 201 are important for correct anatomical assignment of the individual lines. Instead of the markers, however, a sensor measuring the table top displacement could also be used for this purpose. However, such position detection can be dispensed with when, using the image processing method known from DE-OS 41 02 729, the successive, adjoining areas of overlapping X-ray images are identified and combined, that is to say separately for the mask image and the contrast image.

The subtraction image in accordance with the invention represents a static image of the vessels filled with contrast medium. However, reproduction of dynamic processes can also be achieved in a customary manner by storing a sequence of overlapping X-ray images supplied by the AD converter. These may be the same X-ray images used to acquire the contrast image or the mask image, but also, if necessary, additional, automatically formed X-ray images or X-ray images produced by the user in given positions. The memory 20, denoted by broken lines, serves to store this image sequence. When the image processing and control unit 10 is constructed accordingly, this memory may be connected to this unit, as denoted by a broken line; connection to one of the units 11 or 12 would also be possible.

I claim:

1. A method for peripheral angiography in which the examination zone (1, 2) and an X-ray imaging system (3, 4) for generating X-ray images consisting of lines are displaced relative to one another, X-ray images of neighbouring parts of the examination zone being formed in different positions, a contrast image and a mask image being acquired from the X-ray images and the contrast image and the mask image being subtracted from one another, characterized in that after injection of contrast medium the displacement is controlled so that the contrast medium bolus remains reproduced in the X-ray images, and that the contrast image is acquired from X-ray image lines which already reproduce the contrast medium whereas the mask image is acquired from the parts of the X-ray images which do not yet reproduce the contrast medium.

2. An arrangement for carrying out the method claimed in claim 1, comprising a patient table (2), an X-ray imaging system (3, 4) for forming X-ray images, and a drive (7) for producing a relative displacement between the X-ray imaging system and the patient table, or parts thereof, characterized in that it comprises
control means for controlling the instant of exposure (9) and/or of drive (7) so that the contrast medium bolus is reproduced in the X-ray images,
a first memory (17) for storing lines without contrast medium and a second memory (16) for storing lines with contrast medium, and
a unit (10) which forms the mask image from the image lines in the first memory and the contrast image from the image lines in the second memory.

3. An arrangement as claimed in claim 2, characterized in that there are provided a display unit (14) for observing the contrast medium flow, and also means (15) for control of the drive (7) and/or the exposure instant by the user.

4. An arrangement as claimed in claim 2, characterized in that the unit (10) comprises image interpretation means for detecting the contrast medium boundary, or for detecting lines with and lines without contrast medium.

5. An arrangement as claimed in claim 2, characterized in that there are provided means for determining the contrast medium speed from successive X-ray images and for determining the exposure instant and/or the speed of the drive for the next X-ray exposure.

6. An arrangement as claimed in claim 2, characterized in that in the beam path of the X-ray imaging system there are provided markers (201,202) which can be reproduced in an X-ray image.

* * * * *